United States Patent [19]

Mardiguian

[11] 4,440,926
[45] Apr. 3, 1984

[54] HEPARIN ESTERS AND PROCESSES FOR THEIR PREPARATION

[75] Inventor: Jean S. Mardiguian, La Varenne Saint-Hilaire, France

[73] Assignee: Pharmindustrie, Gennevilliers, France

[21] Appl. No.: 258,811

[22] Filed: Apr. 29, 1981

[30] Foreign Application Priority Data

May 14, 1980 [FR] France ................................. 80 10792

[51] Int. Cl.³ ............................................. C08B 37/10
[52] U.S. Cl. ....................................... 536/21; 424/183
[58] Field of Search ........................................... 536/21

[56] References Cited

U.S. PATENT DOCUMENTS

| | | | |
|---|---|---|---|
| 3,065,140 | 11/1962 | Velluz et al. ........................... | 536/21 |
| 3,210,250 | 10/1965 | Bucourt ................................. | 536/21 |
| 3,232,837 | 2/1966 | Nomine et al. ....................... | 536/21 |
| 3,506,642 | 4/1970 | Koh et al. ............................. | 424/183 |
| 3,835,112 | 9/1974 | Mardiguian et al. ................. | 536/21 |
| 3,891,622 | 6/1975 | Mardiguian et al. ................. | 536/21 |
| 4,331,697 | 5/1982 | Kudo et al. ........................... | 536/21 |

FOREIGN PATENT DOCUMENTS

| | | |
|---|---|---|
| 1768806 | 3/1972 | Fed. Rep. of Germany . |
| 2739M | 8/1964 | France . |
| 2267111 | 11/1975 | France . |

OTHER PUBLICATIONS

"Chem. Abst." vol. 77, 1972, P 121990w.

*Primary Examiner*—Johnnie R. Brown

*Attorney, Agent, or Firm*—Beveridge, DeGrandi & Kline

[57] ABSTRACT

Esters of heparin, which are derived from heparin by replacement of the carboxyl groups of heparin by groups of the formula:

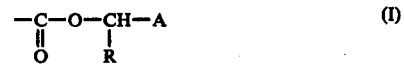

in which R is a hydrogen atom or a methyl group and A is a hydrogen atom or a methyl, phenyl,

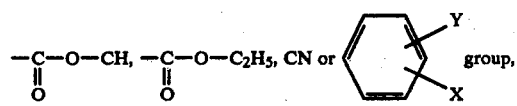

X representing a chlorine atom or a nitro, alkyl containing 1 to 4 carbon atoms or methoxy group and Y representing a hydrogen or chlorine atom, the replacement being a partial or total replacement when A is other than a hydrogen atom or a methyl or phenyl group and the replacement being a partial replacement corresponding to a 10% to 90% esterification percentage of the carboxyl groups when A is a hydrogen atom or a methyl or phenyl group, and the alkali metal, alkaline earth metal, magnesium, quaternary ammonium and amine salts of the said esters. These compounds are intermediate products for preparing medicaments.

15 Claims, No Drawings

HEPARIN ESTERS AND PROCESSES FOR THEIR PREPARATION

The present invention relates to new esters of heparin and their alkali metal, alkaline earth metal, magnesium, quaternary ammonium or amine salts. These compounds may be used as intermediate products for the preparation of medicaments.

Total methyl and benzyl esters of heparin are already known (see British Pat. No. 973,894 and French Medicament Pat. No. 2,739.M), the latter corresponding to U.S. Pat. No. 3,210,250. Heparin esters resulting from the partial or total replacement of the carboxylic groups of the heparin structure by the groups:

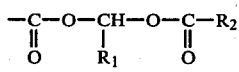

($R_1 = H$ or $CH_3$; $R_2 =$ alkyl containing 1-4 carbon atoms);

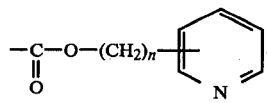

($n = 1, 2$ or $3$);

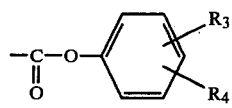

($R_3, R_4 = H, NO_2, COOH$, alkyloxycarbonyl); and

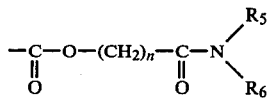

($n = 1, 2$ or $3$; $R_5, R_6 =$ alkyl containing 1-4 carbon atoms) are also known (see British Pat. No. 1,501,095 and French Pat. No. 2,150,724, the latter corresponding to U.S. Pat. No. 3,891,622). These esters are for the most part anticoagulants with a prolonged action.

The heparin esters according to the present invention are derived from heparin by the replacement of the carboxyl groups of the heparin structure by groups of the formula:

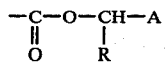  (I)

in which R is a hydrogen atom or a methyl group and A is a hydrogen atom or a methyl, phenyl,

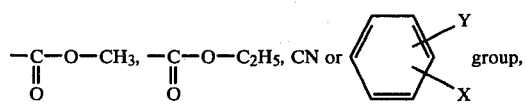 group,

X representing a chlorine atom or a nitro, alkyl containing 1 to 4 carbon atoms or methoxy group and Y representing a hydrogen or chlorine atom, the replacement being a partial or total replacement when A is other than a hydrogen atom or a methyl or phenyl group and the replacement being a partial replacement corresponding to a 10% to 90% esterification percentage of the carboxyl groups when A is a hydrogen atom or a methyl or phenyl group.

In the above formula (I), R is preferably a hydrogen atom and A is preferably a

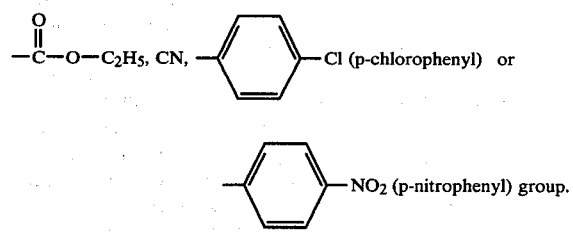

$NO_2$ (p-nitrophenyl) group.

The alkali metal, alkaline earth metal, magnesium, quaternary ammonium and amine salts of the preceding esters also form part of the invention. Alkali metal salts to be mentioned in particular are the sodium salts and as alkaline earth metal salts may be mentioned the calcium salts.

Amine salts may be salts of tertiary amines, especially the salts of triethylamine, pyridine or imidazole. Quaternary ammonium salts may be the long chain alkyl or aralkyl quaternary ammonium salts wherein the alkyl contains from 2 to 20 carbon atoms, particularly dodecyltrimethylammonium and benzethonium salts, and cetylpyridinium salts.

The heparin esters according to the present invention may be non-selective esters or selective esters. By non-selective esters are intended heparin esters wherein the carboxyl groups of D-glucuronic acid, unsulfated L-iduronic acid and sulfated L-iduronic acid linkages are indiscriminately esterified. By selective esters are intended heparin esters wherein are esterified, partially or wholly, either only the carboxyl groups of the D-glucuronic acid linkages or only the carboxyl groups of the D-glucuronic acid and unsulfated L-iduronic acid linkages, or only the carboxyl groups of the unsulfated L-iduronic acid and sulfated L-iduronic acid linkages, or only the carboxyl groups of the sulfated L-iduronic acid linkages.

The non-selective heparin esters according to the invention may be prepared as follows:

(a) There is first prepared an acid salt of heparin by replacing the acid sulfate groups of the heparin by quaternary ammonium sulfate groups, the carboxyl groups of heparin remaining in free form. In order to obtain such an acid salt of heparin it is sufficient, for example, to treat a neutral salt of heparin, in which the sulfate and carboxyl groups of heparin have been replaced respectively by quaternary ammonium sulfate groups and quaternary ammonium carboxylate groups, with a carboxylic cation exchanger in acid form.

(b) An alcohol of the formula:

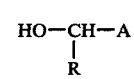  (II)

in which R and A have the same significance as in formula (I) is made to act on said acid salt of heparin.

The reaction of stage (b) is effected at a temperature from $-5°$ C. to $+10°$ C. in an inert solvent (for example dimethylformamide or methylene chloride), in the presence of a condensation agent of the carbodiimide type (for example dicyclohexylcarbodiimide). The esterification percentage of the carboxyl groups depends on the operational conditions (nature of the alcohol of formula II, length of reaction and the proportions of the reactants).

The esters of heparin obtained at stage (b), of which the sulfate groups are in the quaternary ammonium sulfate form, can be converted into an alkali metal, alkaline earth metal, magnesium or amine salt or into a heparin ester not in salt form by methods known per se. For example, to prepare the alkali metal, alkaline earth metal or magnesium salts, the corresponding acetate may be allowed to act on the heparin ester in the quaternary ammonium sulfate form. To prepare the amine salts, sodium acetate is reacted with the heparin ester in the quaternary ammonium sulfate form so as to form the sodium salt, then this sodium salt is passed over a sulfonic cation exchanger in the form $H^+$ so as to form the acid, said acid is salified by the amine and the product formed is isolated by lyophilization or precipitation by addition of acetone.

The non-selective heparin esters according to the invention are prepared preferably by reaction of a neutral quaternary ammonium salt or amine salt of the heparin, that is, of a salt of heparin in which all the acid functions of the heparin have been salified with a halogen derivative of the formula:

(III)

in which Hal indicates a chlorine, bromine or iodine atom and R and A have the same significance as in formula (I). The reaction may be shown diagrammatically as follows:

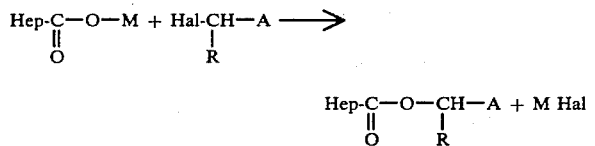

Hep and M indicate respectively in the above formulae a heparin residue and a quaternary ammonium or amine radical.

The reaction of the neutral quaternary ammonium or amine salt of the heparin with the halogen derivative of formula (III) is effected, in solution or in suspension in an inert solvent, at a temperature between $-20°$ C. and $+60°$ C. As inert solvent may be particularly mentioned dimethylformamide, chloroform, hexamethylphosphorylamide, methylene chloride, dimethylsulfoxide, tetrahydrofuran and acetone. The esterification percentage of the carboxyl groups depends on the operational conditions (nature of the halogenated derivative of formula (III) and of the solvent, length of reaction, proportion of the reactants, temperature, etc.).

The heparin ester obtained, of which the sulfate groups and possibly the non-esterified carboxyl groups are in the quaternary ammonium or amine sulfate or carboxylate form, can be converted into an alkali metal, alkaline earth metal or magnesium salt or into a heparin ester not in salt form by methods known per se, in particular those described above.

The partial or total esters obtained by the processes previously described can be converted by incomplete hydrolysis into esters having a lesser degree of esterification. Such an incomplete hydrolysis can be effected, for example, by subjecting the said partial or total esters to the action of an aqueous solution of an alkali metal carbonate, especially disodium carbonate, for 30 minutes to 6 hours, at a temperature of $5°$ C. to $25°$ C.

The selective heparin esters according to the invention wherein are esterified, partially or wholly, either only the carboxyl groups of the D-glucuronic acid linkages or only the carboxyl groups of the D-glucuronic acid and unsulfated L-iduronic acid linkages are obtained by reacting a halogen derivative of the above formula (III) with an acid quaternary ammonium salt of heparin in which are salified, in addition to the sulfate groups, either only the carboxyl groups of the D-glucuronic acid linkages, or only the carboxyl groups of the D-glucuronic acid and unsulfated L-iduronic acid linkages, the other carboxyl groups being in the free acid form. The reaction is carried out under the same conditions as the reaction of the halogen derivative of the formula (III) with a neutral quaternary ammonium salt of heparin.

The acid quaternary ammonium salts of heparin in which are salified in addition to the sulfate groups, only the carboxyl groups of the D-glucuronic acid linkages, are prepared by reacting a quaternary ammonium salt with heparin in an aqueous medium, the pH of which is between 3 and 4.

The acid quaternary ammonium salts of heparin in which are salified, in addition to the sulfate groups, only the carboxyl groups of the D-glucuronic acid and unsulfated L-iduronic acid linkages, are obtained by reacting a quaternary ammonium salt with heparin in an aqueous medium, the pH of which is low enough to form the quaternary ammonium salt of heparin wherein only the sulfate groups are salified (practically, the pH is from 2 to 2.5), then selectively neturalizing the carboxyl groups of the D-glucuronic acid and unsulfated L-iduronic acid linkages of the product so obtained by addition of a determined amount of quaternary ammonium hydroxide in a dimethylformamide medium. The amount of quaternary ammonium hydroxide to be added is deduced from the neutralization curve in a dimethylformamide medium for a sample of the product having a known weight.

The selective heparin esters according to the invention wherein are esterified, partially or wholly, either only the carboxyl groups of the sulfated L-iduronic acid linkages or only the carboxyl groups of the unsulfated L-iduronic acid and sulfated L-iduronic acid linkages, are prepared by reacting an alcohol of formula (II) with heparin, in an aqueous medium, in presence of a water-soluble condensation agent of the carbodiimide type such as, for example, 1-ethyl-3-(3-dimethyl-aminopropyl)-carbodiimide, the pH of the medium being adjusted to a value in the range of 3.5–4.5 in the first case and in the range of 2–3 in the second case. As alcohol of formula (II) which can be used may be particularly mentioned methanol and ethanol, in which case there is obtained respectively a selective methyl ester of heparin and a selective ethyl ester of heparin.

The compounds according to the invention, when subjected to the action of a 0.1 N to 0.5 N aqueous solution of sodium hydroxide at a temperature of from 20° C. to 60° C. or to the action of an organic base such as 1,5-diaza-bicyclo[4.3.0]non-5-ene in methylene chloride, undergo a depolymerization which leads to mixtures of sulfated polysaccharides having an average molecular weight less than that of heparin. These mixtures are anticoagulant and antithrombotic agents useful for the prevention and treatment of thromboses.

The following examples illustrate the invention without it being limited thereby. Examples 1 to 12 relate to the preparation of non-selective esters, and Examples 13 to 20 to the preparation of selective esters.

The neutral benzethonium salt of heparin or benzethonium heparinate used as starting product in Examples 1, 6, 7 and 8 is taken from a heparin from pig's intestine having the following characteristics:
Weight: Mean molecular weight: 16,000 daltons.
Specific rotatory power in aqueous solution at 20° C.: $[\alpha]_D^{20}$: +41°.
Codex anticoagulant activity: 157 u.i./mg.

The neutral benzethonium salt of heparin or benzethonium heparinate used as starting product in Examples 2, 3, 4 and 5 is taken from a heparin of ox intestines having the following characteristics:
Weight: Mean molecular weight: 11,400 daltons.
Specific rotatory power in aqueous solution at 20° C.: $[\alpha]_D^{20}$: +37°.
Codex anticoagulant activity: 128 u.i./mg.

The neutral benzethonium salt of heparin or benzethonium heparinate used as starting product in Examples 10 to 12 is taken from a heparin of pig's mucus having a weight average molecular weight 16,000 daltons, a specific rotatory power in aqueous solution at 20° C. of +44° and a codex anticoagulant activity 180 u.i./mg.

The sodium salt of heparin used as starting product in Examples 13 to 20 corresponds to the above heparin from pig's mucus.

EXAMPLE 1

30 g of (4-chloro)-benzyl chloride are added to a solution of 30 g of benzethonium heparinate in 600 ml of dimethylformamide. After solution, the substances are left in contact for 60 hours at the ambient temperature (about 20° C.)., then 600 ml of 10% solution of sodium acetate in methanol are added. The precipitate formed is separated by filtration, washed with methanol and dried in vacuo. 10.75 g of the (4-chloro)-benzyl ester of heparin are thus obtained in the form of the sodium salt.

The product obtained shows in aqueous solution a maximum absorption in ultra-violet at 220 nm. The optical density at this wave-length of an aqueous solution containing 5 mg of product in 100 ml of water is 0.605 for a thickness of 1 cm.

EXAMPLE 2

5 g of ethyl chloroacetate are added to a solution of 5 g of benzethenium heparinate in 125 ml of dichloromethane and, after solution, the substances are left in contact for 3 days at the ambient temperature. The solvent is evaporated under vacuum, the residue is taken up in 75 ml of dimethylformamide and 75 ml of a 10% solution of sodium acetate in methanol are added. The precipitate, separated by filtration, is washed with methanol, then dried in vacuo. 1.72 g of the carbethoxymethyl ester of heparin are thus obtained in the form of the sodium salt.

EXAMPLE 3

10 g of (4-chloro)-benzyl chloride are added to a solution of 10 g of benzethonium heparinate in 250 ml of dichloromethane and are dissolved by stirring. The solution is left for 24 hours at the ambient temperature, then the solvent is evaporated under vacuum. The residue is taken up in 150 ml of dimethylformamide and 150 ml of 10% solution of sodium acetate in methanol are added. After filtration, washing with methanol and drying in vacuo of the precipitate formed, 3.84 g of the (4-chloro)-benzyl ester of heparin are obtained in the form of the sodium salt.

The product obtained shows in aqueous solution a maximum absorption in ultra-violet at 220 nm. The optical density at this wave-length of an aqueous solution containing 5 mg of product in 100 ml of water is 0.337 for a thickness of 1 cm.

EXAMPLE 4

5 g of (4-nitro)-benzyl chloride are added to a solution of 5 g of benzethonium heparinate in 125 ml of dichloromethane, and are dissolved by stirring. The solution is then left for 3 days at the ambient temperature, then the solvent is evaporated in vacuo and the residue is dissolved in 75 ml of diemthylformamide. The ester formed is precipitated by addition of 75 ml of a 10% solution of sodium acetate in methanol. The precipitate is collected by filtration, washed with methanol and dried in vacuo. 1.89 g of the (4-nitro)-benzyl ester of heparin are thus obtained in the form of the sodium salt.

The product obtained shows in aqueous solution a maximum absorption in ultra-violet at 272 nm. The optical density at this wave-length of an aqueous solution containing 5 mg of product in 100 ml of water is 0.408 for a thickness of 1 cm.

EXAMPLE 5

10 g of (4-chloro)-benzyl chloride are added to a solution of 10 g of benzethonium heparinate in 250 ml of dichloromethane and are dissolved by stirring. The solution is left at the ambient temperature for 24 hours, then the solvent is evaporated under vacuum. The residue is taken up by 200 ml of ether and the precipitate formed is isolated by filtration. 10 g of the (4-chloro)-benzyl ester of heparin are thus obtained in the form of the benzethonium salt.

EXAMPLE 6

120 g of (4-chloro)-benzyl chloride are added to a solution of 120 g of benzethonium heparinate in 2.5 l of dimethylformamide and are dissolved by stirring. The solution is then left at the ambient temperature for 60 hours, then 2.4 l of a 10% solution of sodium acetate in methanol is added. The precipitate formed is separated by filtration, washed with methanol and dried under vacuum. 46 g of the (4-chloro)-benzyl ester of heparin are thus obtained in the form of the sodium salt.

The product obtained shows in aqueous solution a maximum absorption in ultra-violet at 220 nm. The optical density at this wave-length of an aqueous solution containing 5 mg of product in 100 ml of water is 0.573 for a thickness of 1 cm.

EXAMPLE 7

30 g of ethyl chloroacetate are added to a solution of 30 g of benzethonium heparinate in 600 ml of dimethylformamide. After solution, the mixture is left in contact for 60 hours at the ambient temperature, then 600 ml of a 10% solution of sodium acetate in methanol are added. The precipitate formed is separated by filtration, washed with methanol and dried under vacuum. 10.78 g of the carbethoxymethyl ester of heparin are thus obtained in the form of the sodium salt.

EXAMPLE 8

5 g of chloracetonitrile are added to a solution of 5 g of benzethonium heparinate in 125 ml of dichloromethane and are dissolved by stirring. The solution is left for 48 hours at the ambient temperature, then the solvent is evaporated under vacuum. The residue is dissolved in 75 ml of dimethylformamide and 75 ml of 10% solution of sodium acetate in methanol are added. The precipitate formed is separated by filtration, washed with methanol and dried under vacuum. 1.03 g of the cyanomethyl ester of heparin are thus obtained in the form of the sodium salt.

EXAMPLE 9

3 g of the (4-chloro)-benzyl ester of heparin obtained in Example 6 are dissolved with stirring in 120 ml of a 10% aqueous solution of disodium carbonate. After stirring for two hours at a temperature of 20° C. to 25° C., the pH of the solution is brought to 6 by addition of an N aqueous solution of hydrochloric acid, then a volume of methanol equal to twice the volume of the aqueous solution is added. The precipitate formed is isolated by filtration and 2.1 g of (4-chloro)-benzyl ester of heparin are thus obtained.

The product obtained shows in aqueous solution a maximum absorption in ultra-violet at 220 nm. The optical density at this wave-length of an aqueous solution at 5 mg of product in 100 ml of water is 0.260 for a thickness of 1 cm.

EXAMPLE 10

10 ml of benzyl chloride are added to a solution of 10 g of benzethonium heparinate in 50 ml of dichloromethane. After solution, the mixture is left for 96 hours at the ambient temperature, then 50 ml of a 10% solution of sodium acetate in methanol are added. The precipitate formed is collected by filtration, washed with methanol and taken up with 20 ml of a 10% aqueous solution of sodium chloride. After addition of 50 ml of methanol, 3.62 g of benzyl ester of heparin are isolated in the form of the sodium salt.

Characteristics of the product obtained:

Esterification percentage of the carboxyl groups: 70%.

Absorption spectrum in ultra-violet of an aqueous solution containing 50 μg/ml:

Absorption maxima: 195 nm and 205 nm.

Optical density at 205 nm for a 1 cm thickness: 0.359.

EXAMPLE 11

0.9 ml of methyl iodide are added to a solution of 10 g of benzethonium heparinate in 50 ml of dichloromethane and the mixture is left in contact for 24 hours at the ambient temperature. Then 50 ml of a 10% solution of sodium acetate in methanol are added. The precipitate formed is isolated by filtration, washed with methanol and dissolved in 20 ml of a 10% aqueous solution of sodium chloride. After addition of 50 ml of methanol, 3.38 g of methyl ester of heparin, in the form of the sodium salt, are collected by filtration. In this product, the esterification percentage of the carboxyl groups is 55%.

EXAMPLE 12

1 ml of ethyl iodide is added to a solution of 10 g of benzethonium heparinate in 50 ml of dichloromethane and the solution is left for 24 hours at the ambient temperature. Then 50 ml of a 10% solution of sodium acetate in methanol are added. The precipitate formed is isolated by filtration, washed with methanol and dissolved in 20 ml of a 10% aqueous solution of sodium chloride. 50 ml of methanol are added and 3.45 g of ethyl ester of heparin in the form of the sodium salt, are collected by filtration. In this product the esterification percentage of the carboxyl groups is 45%.

EXAMPLE 13

2.5 ml of acetic acid then, slowly and with stirring, 150 ml of a 10% aqueous solution of benzethonium chloride are added to a solution of 10 g of heparin (sodium salt) in 40 ml of water. The precipitate formed is collected by centrifugation, washed with water and dried. 19.67 g of benzethonium acid heparinate are obtained.

5 g of the above product are dissolved in 100 ml of dimethylformamide and 5 g of (4-chloro)-benzyl chloride are added. The reactants are left in contact for 48 hours at the ambient temperature, then 100 ml of a 10% solution of sodium acetate in methanol are added. The precipitate formed is isolated by filtration, washed with methanol and dried under vacuum. 2.11 g of (4-chloro)-benzyl ester of heparin are thus obtained in the form of the sodium salt.

Characteristics of the product obtained:

Esterification percentage of the carboxyl groups: 22%.

Absorption spectrum in ultra-violet of an aqueous solution containing 50 μg/ml:

Absorption maxima: 196 nm and 220 nm.

Optical density at 220 nm for a 1 cm thickness: 0.120.

EXAMPLE 14

2.5 ml of acetic acid then, slowly and with stirring, 150 ml of a 10% aqueous solution of benzethonium chloride are added to a solution of 10 g of heparin (sodium salt) in 40 ml of water. The precipitate formed is collected by centrifugation, washed with water and dried. 19.67 g of benzethonium acid heparinate are obtained.

5 g of the above product are dissolved in 25 ml of dichloromethane and 2.2 ml of methyl iodide are added. The solution is maintained for 24 hours at the ambient temperature, away from light. 75 ml of a 10% solution of sodium acetate in methanol are added. The precipitate formed is isolated by filtration, washed with methanol and dried under vacuum. 2 g of methyl ester of heparin are obtained in the form of the sodium salt. In this product the esterification percentage of the carboxyl groups is 22%.

EXAMPLE 15

2.5 ml of formic acid then, slowly and with stirring, 150 ml of a 10% aqueous solution of benzethonium chloride are added to a solution of 10 g of heparin (sodium salt) in 40 ml of water. The precipitate is collected by centrifugation, washed with water and dried under vacuum. 20.5 g of benzethonium acid heparinate are thus obtained.

10 g of the above product are dissolved in 200 ml of dimethylformamide, then 27.4 ml of a 0.1 N solution of tetrabutylammonium hydroxide in a n-propanol/methanol mixture are added. After the addition of 10 g of (4-chloro)-benzyl chloride, the solution is left for five days at the ambient temperature. 250 ml of a 10% solution of sodium acetate in methanol are added. 4.50 g of (4-chloro)-benzyl ester of heparin are isolated by filtration, in the form of the sodium salt.

Characteristics of the product obtained:

Esterification percentage of the carboxyl groups: 45%.

Absorption spectrum in ultra-violet of an aqueous solution containing 50 μg/ml:

Absorption maxima: 196 nm and 220 nm.

Optical density at 220 nm for a 1 cm thickness: 0.265.

EXAMPLES 16 TO 20

0.300 g of 1-ethyl-3-(3-dimethylaminopropyl)-carbodiimide are added to a solution of 0.600 g of heparin (sodium salt) in 7 ml of water, the pH of which has been adjusted to the desired value (see the table below) by the addition of an N aqueous solution of hydrochloric acid.

After a one hour contact at the ambient temperature, 2.5 ml of an aqueous solution of sodium chloride containing 200 g/l, then 15 ml of methanol are added. The precipitate formed is collected by filtration, washed with methanol and dried under vacuum. Methyl esters of heparin, in the form of the sodium salt, are thus obtained. The esterification percentage of the carboxyl groups is given in the following table.

TABLE

| Example | pH of the Aqueous Solution of Heparin | Weight of Ester Obtained | Esterification Percentage |
|---|---|---|---|
| 16 | 2.5 | 0.565 g | 77% |
| 17 | 3 | 0.647 g | 70% |
| 18 | 3.5 | 0.527 g | 50% |
| 19 | 4 | 0.545 g | 31% |
| 20 | 4.5 | 0.550 g | 19% |

What is claimed is:

1. Esters of heparin, which are derived from heparin by replacement of the carboxyl groups of heparin by groups of the formula:

 (I)

in which R is hydrogen or methyl and A is hydrogen, methyl, phenyl,

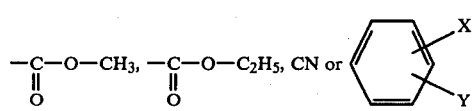

X representing chlorine, nitro, alkyl containing 1 to 4 carbon atoms or methoxy and Y representing hydrogen or chlorine, the replacement being a partial or total replacement when A is other than hydrogen, methyl or phenyl, and, when A is hydrogen, methyl or phenyl, the replacement being a partial replacement corresponding to a 10% to 90% esterification percentage of the carboxyl groups and the esters being selective esters wherein are esterified, partially or wholly, either only the carboxyl groups of the D-glucuronic acid linkages, only the carboxyl groups of the D-glucuronic acid and unsulfated L-iduronic acid linkages, only the carboxyl groups of the unsulfated L-iduronic acid and sulfated L-iduronic acid linkages, or only the carboxyl groups of the sulfated L-iduronic acid linkages, and the alkali metal, alkaline earth metal, magnesium, quaternary ammonium and triethylamine, pyridine and imidazole salts of said esters.

2. Heparin esters according to claim 1 wherein, in the groups of formula (I), R is hydrogen and A is

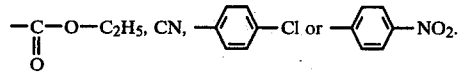

3. Heparin esters according to claim 1 which are non-selective esters in which A is other than hydrogen, methyl or phenyl.

4. Heparin esters according to claim 1 which are selective esters in which are esterified, partially or wholly, only the carboxyl groups of the D-glucuronic acid linkages.

5. Heparin esters according to claim 1 which are selective esters in which are esterified, partially or wholly, only the carboxyl groups of the D-glucuronic acid linkages and unsulfated L-iduronic acid linkages.

6. Heparin esters according to claim 1 which are selective esters in which are esterified, partially or wholly, only the carboxyl groups of the unsulfated L-iduronic acid and sulfated L-iduronic acid linkages.

7. Heparin esters according to claim 1 which are selective esters in which are esterified, partially or wholly, only the carboxyl groups of the sulfated L-iduronic acid linkages.

8. Alkali metal salts of esters according to claim 1, 2, 3, 4, 5, 6 or 7 in which the alkali metal cation is sodium.

9. Alkaline earth metal salts of esters according to claim 1, 2, 3, 4, 5, 6 or 7 in which the alkaline earth metal cation is calcium.

10. Magnesium salts of esters according to claim 1, 2, 3, 4, 5, 6 or 7.

11. Quaternary ammonium salts of esters according to claim 1, 2, 3, 4, 5, 6 or 7 in which the quaternary ammonium cation is the benzethonium cation.

12. A process for preparing the compounds according to claim 6 wherein an alcohol of the formula:

 (II)

wherein R and A have the same definition as in formula (I), is reacted with heparin in an aqueous medium having a pH of from 2 to 3 in the presence of a water-soluble condensation agent of the carbodiimide type.

13. A process for preparing the compounds according to claim 7 wherein an alcohol of the formula:

 (II)

in which R and a have the same definition as in formula (I), is reacted with heparin in an aqueous medium having a pH of from 3.5 to 4.5 in the presence of a water-soluble condensation agent of the carbodiimide type.

14. A process for preparing the compounds according to claim 4, in which:
(a) a quaternary ammonium salt is reacted with heparin in an aqueous medium, the pH of which is between 3 and 4; and
(b) the so obtained acid quaternary ammonium salt of heparin in which are salified, in addition to the sulfate groups, only the carboxyl groups of the D-glucuronic acid linkages is reacted with a halogen derivative of the formula:

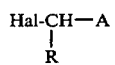

in which Hal is a chlorine, bromine or iodine atom and R and A have the same definition as in formula (I).

15. A process for preparing the compounds according to claim 5, in which:

(a) a quaternary ammonium salt is reacted with heparin in an aqueous medium, the pH of which is from 2 to 2.5;
(b) the carboxyl groups of the D-glucuronic acid and unsulfated L-iduronic acid linkages of the product so obtained are selectively neutralized by addition of a determined amount of quaternary ammonium hydroxide in a dimethylformamide medium; and
(c) the so obtained acid quaternary ammonium salt of heparin in which are salified, in addition to the sulfate groups, only the carboxyl groups of the D-glucuronic acid and unsulfated L-iduronic acid linkages is reacted with a halogen derivative of the formula:

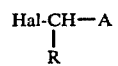

in which Hal is a chlorine, bromine or iodine atom and R and A have the same definition as in formula (I).

* * * * *